(12) United States Patent
Liao et al.

(10) Patent No.: US 10,801,905 B2
(45) Date of Patent: Oct. 13, 2020

(54) GRIP-STRENGTH DEVICE WITH DETECTION FUNCTION

(71) Applicant: GOLDENSUNDA TECHNOLOGY CO., LTD., New Taipei (TW)

(72) Inventors: Chi-Yao Liao, New Taipei (TW); Chun-Feng Huang, New Taipei (TW)

(73) Assignee: GOLDENSUNDA TECHNOLOGY CO., LTD., New Taipei (TW)

( * ) Notice: Subject to any disclaimer, the term of this patent is extended or adjusted under 35 U.S.C. 154(b) by 118 days.

(21) Appl. No.: 16/262,910

(22) Filed: Jan. 31, 2019

(65) Prior Publication Data

US 2020/0173873 A1 Jun. 4, 2020

(30) Foreign Application Priority Data

Nov. 29, 2018 (TW) .............................. 107216222 A (51) Int. Cl.
*G01L 5/00* (2006.01)
*A61B 5/22* (2006.01)
*G06F 3/14* (2006.01)

(52) U.S. Cl.
CPC ............ *G01L 5/0033* (2013.01); *A61B 5/225* (2013.01); *G06F 3/14* (2013.01)

(58) Field of Classification Search
CPC .......... G01L 5/0033; A61B 5/225; G06F 3/14
USPC .......................................................... 73/760
See application file for complete search history.

(56) References Cited

U.S. PATENT DOCUMENTS

| | | | | |
|---|---|---|---|---|
| 9,033,706 B2 * | 5/2015 | Lee | ........................... | A61C 5/50 433/81 |
| 2002/0015024 A1 * | 2/2002 | Westerman | ........... | G06F 3/0235 345/173 |
| 2003/0233069 A1 * | 12/2003 | Gillespie, Jr. | ......... | A61M 5/142 604/131 |
| 2012/0297646 A1 * | 11/2012 | Brault | .................. | A43B 3/0015 36/124 |
| 2019/0041282 A1 * | 2/2019 | Chen | ..................... | G01L 1/2293 |

* cited by examiner

*Primary Examiner* — Max H Noori
(74) *Attorney, Agent, or Firm* — Leong C. Lei (57) ABSTRACT

A grip-strength device with detection function comprises: a grip-strength assembly comprising a first supporting piece, a second supporting piece, a rebounding element, a plurality of detection elements, a circuit element, a pull-force measuring element, and a power-supply element. The user can hold the grip-strength assembly and press the first supporting piece and the second supporting piece; and the force given by the user to the first supporting piece and the second supporting piece is measured by the pull-force measuring element; thereby detecting the user's grip force; or touching the detection elements with both hands, the circuit element will generate the detection current to enter the human body through the detection elements and then returns to the circuit element to detect the muscle mass in the human body; thereby the grip-strength assembly can have the functions of simultaneously detecting the grip strength and the body's muscle mass.

7 Claims, 10 Drawing Sheets

GRIP-STRENGTH DEVICE WITH DETECTION FUNCTION

(a) TECHNICAL FIELD OF THE INVENTION

The present invention provides a grip-strength device with detection function, and especially relates to a grip-strength device with detection function having a grip-strength assembly with multiple detection effects.

(b) DESCRIPTION OF THE PRIOR ART

Generally, if having good fitness habits, the benefits to the human body are quite a lot; in addition to maintaining a good posture but also having a healthy body. It can be seen that everywhere has the gymnasium, having good fitness habits is already quite common in modern people.

And, because of the popularity of fitness concepts, in addition to the old concept of fat and thin, people gradually began to care about the ratio of fat to muscle in the body. Because even two people with two equal heights and weights, the proportions will be different due to body fat and muscle are different, and the different postures and health conditions are formed. For example, some people do not seem to be fat, but because the muscle ratio in the body is quite low and the fat ratio is high, the health condition is worse than the average person. The general method of measuring the ratio of fat and muscle in the body is measured by a body fat meter, which is to introduce a current into the human body; and because the impedance of fat, muscle, bone, and water in the human body is different; the ratio of fat, muscle, bone, and water in the human body can be estimated from the electrical resistance of the current through the human body.

However, the body fat meter on the market currently can only measures the ratio of fat and muscle; which cannot have other measurement functions at the same time.

SUMMARY OF THE INVENTION

In view of the above-mentioned deficiencies, the inventors of this invention collect relevant information, evaluate and consider through multiple parties, and use the years of experience accumulated in this industry to continuously design and modify this invention of grip-strength device with detection function; in addition to measuring the muscle mass in the human body, it can also detect the grip strength.

The main objectives of the present invention are to measure the grip strength by using a pull-force measuring element cooperating with the grip-strength assembly and the circuit element, and to measure the muscle ratio in the body via the detection elements and the circuit element.

In order to achieve the above objectives, the main structure of the present invention comprises: a grip-strength assembly, a plurality of detection elements set on the grip-strength assembly, a pull-force measuring element set on the grip-strength assembly; a circuit element set in the grip-strength assembly; and a power-supply element set in the grip-strength assembly; wherein the grip-strength assembly comprises a first supporting piece, a second supporting piece, and a rebounding element; wherein the first supporting piece and the second supporting piece are connected with each other by using the rebounding element; wherein the pull-force measuring element is set between the first supporting piece and the second supporting piece to measure the grip strength when the first supporting piece and the second supporting piece are displaced with each other.

With the above structure, the user can hold the grip-strength assembly and make the first supporting piece and the second supporting piece move away from each other, and simultaneously transmit the far-moving force to the pull-force measuring element; and the rebounding element gives a rebounding force to the first supporting piece and the second supporting piece after the measurement; thereby achieving the effect of measuring the grip force.

When wanting to measure the muscle mass in the body, the user can touch the detection elements with both hands, and the detection elements will contact the palms of the person; and the circuit element will generate a detection current through the power given by the power-supply element, which the detection current passes through one of the detection elements to enter into the human body, and then returns into the circuit element via the other detection element; such that the ratio of fat, bone, muscle, and water in the human body can be detected through the circuit element cooperating with the detection current; thereby the grip-strength assembly can have the dual functions of measuring the grip force and detecting the muscle mass in the human body.

With the above techniques, the present invention can break through the problem of the single detection function of the conventional body fat meter, and so as to achieve the practicality and progressiveness with the above advantages.

DETAILED DESCRIPTION OF THE PREFERRED EMBODIMENTS

The following descriptions are exemplary embodiments only, and are not intended to limit the scope, applicability or configuration of the invention in any way. Rather, the following detailed description provides a convenient illustration for implementing exemplary embodiments of the invention. Various changes to the described embodiments may be made in the function and arrangement of the elements described without departing from the scope of the invention as set forth in the appended claims.

The foregoing and other aspects, features, and utilities of the present invention will be best understood from the following detailed description of the preferred embodiments when read in conjunction with the accompanying drawings.

Figure 1:
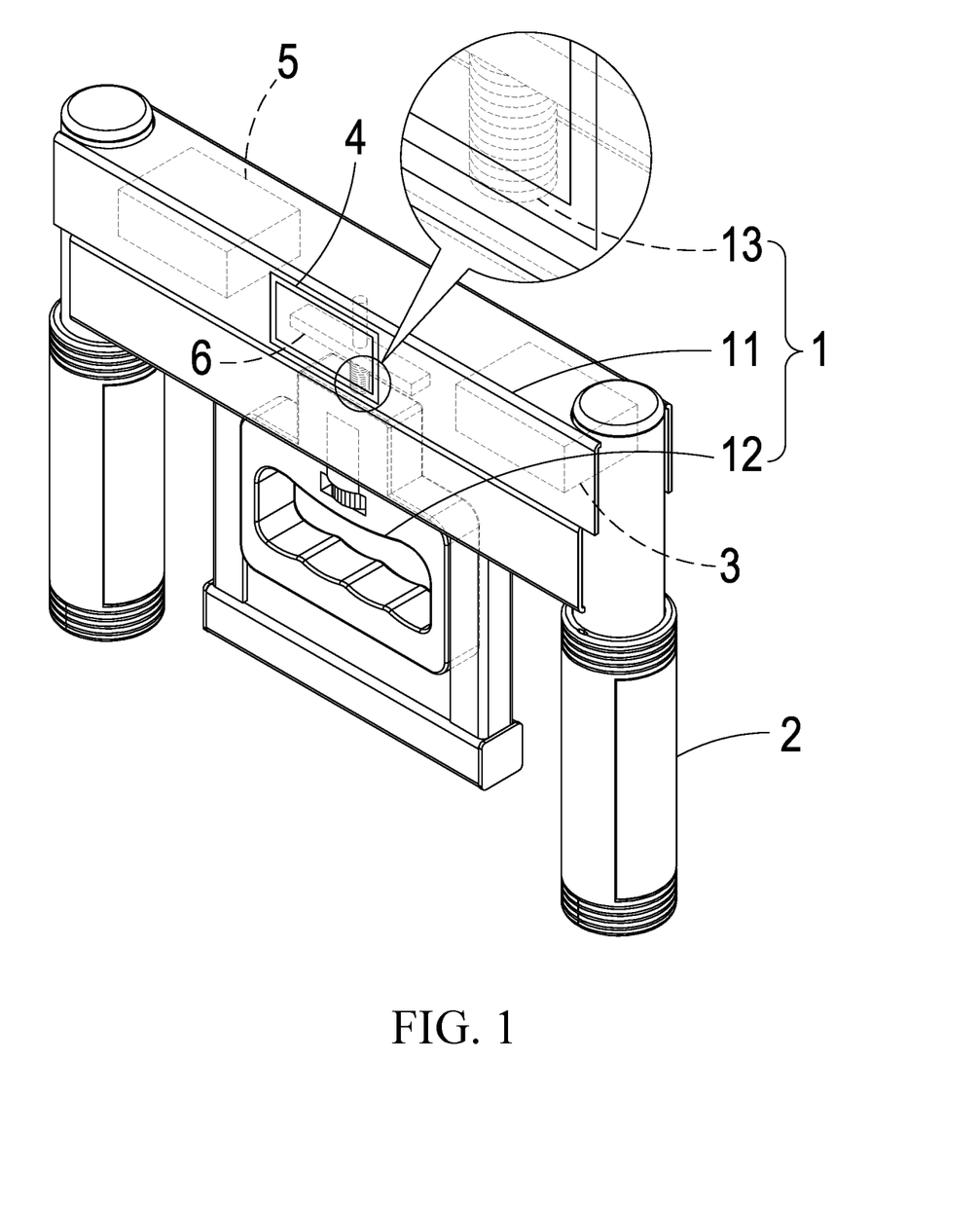
FIG. 1 is a stereo perspective view of the preferred embodiment of the present invention.
Figure 2:
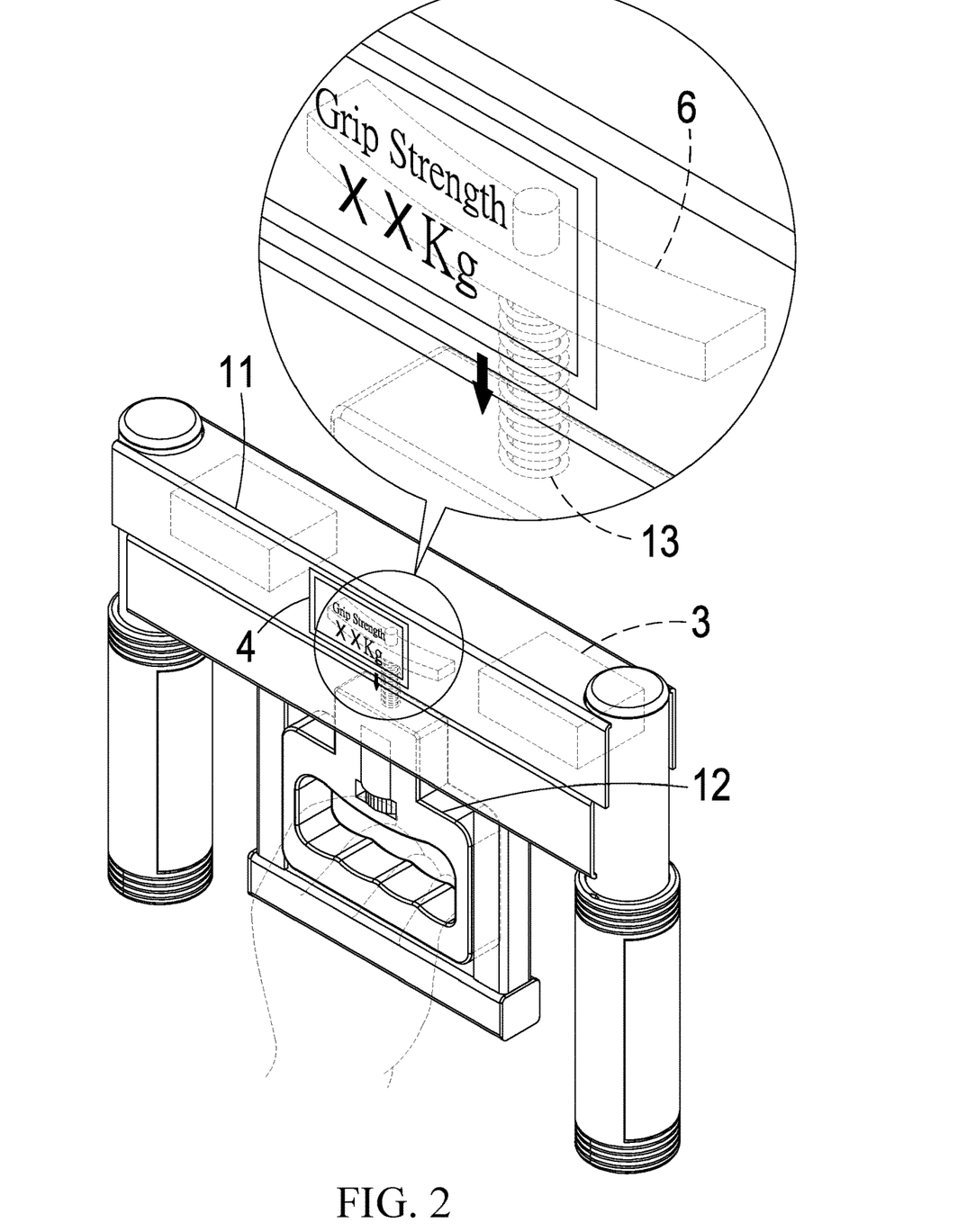
FIG. 2 is a pulling schematic diagram of the preferred embodiment of the present invention.
Figure 3:
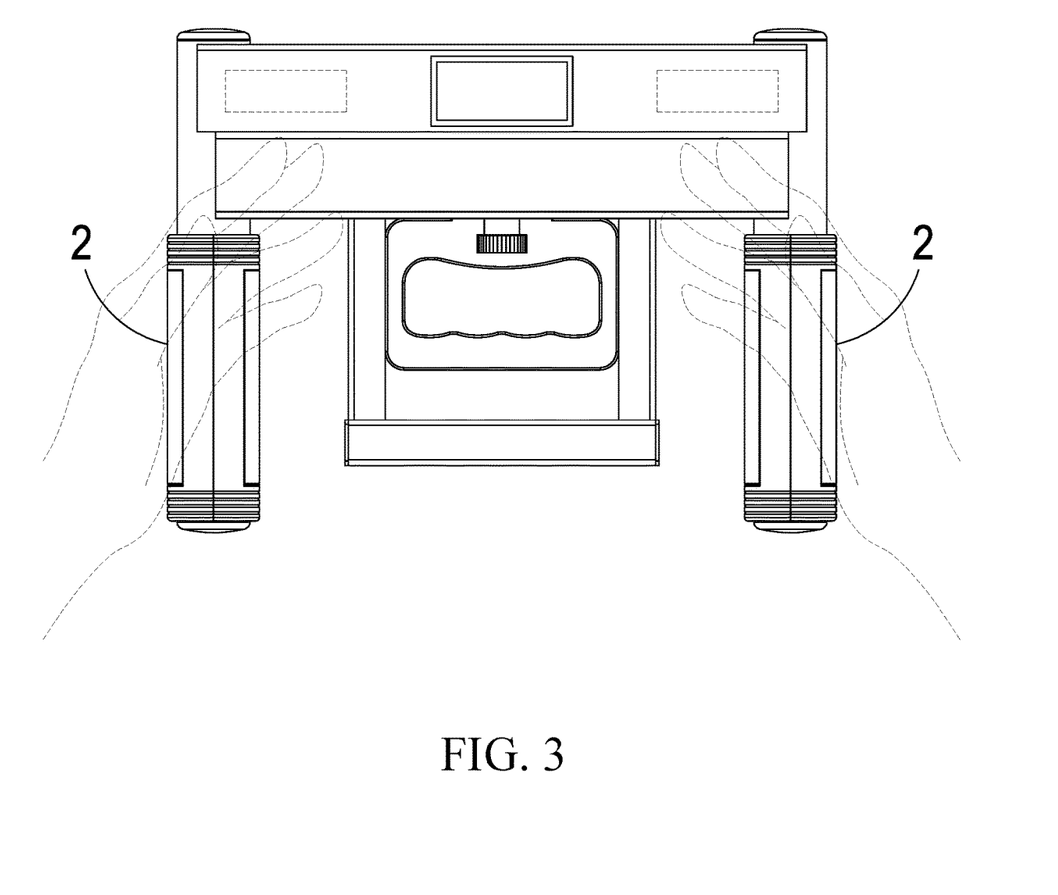
FIG. 3 is a touching schematic diagram of the preferred embodiment of the present invention.
Figure 4:
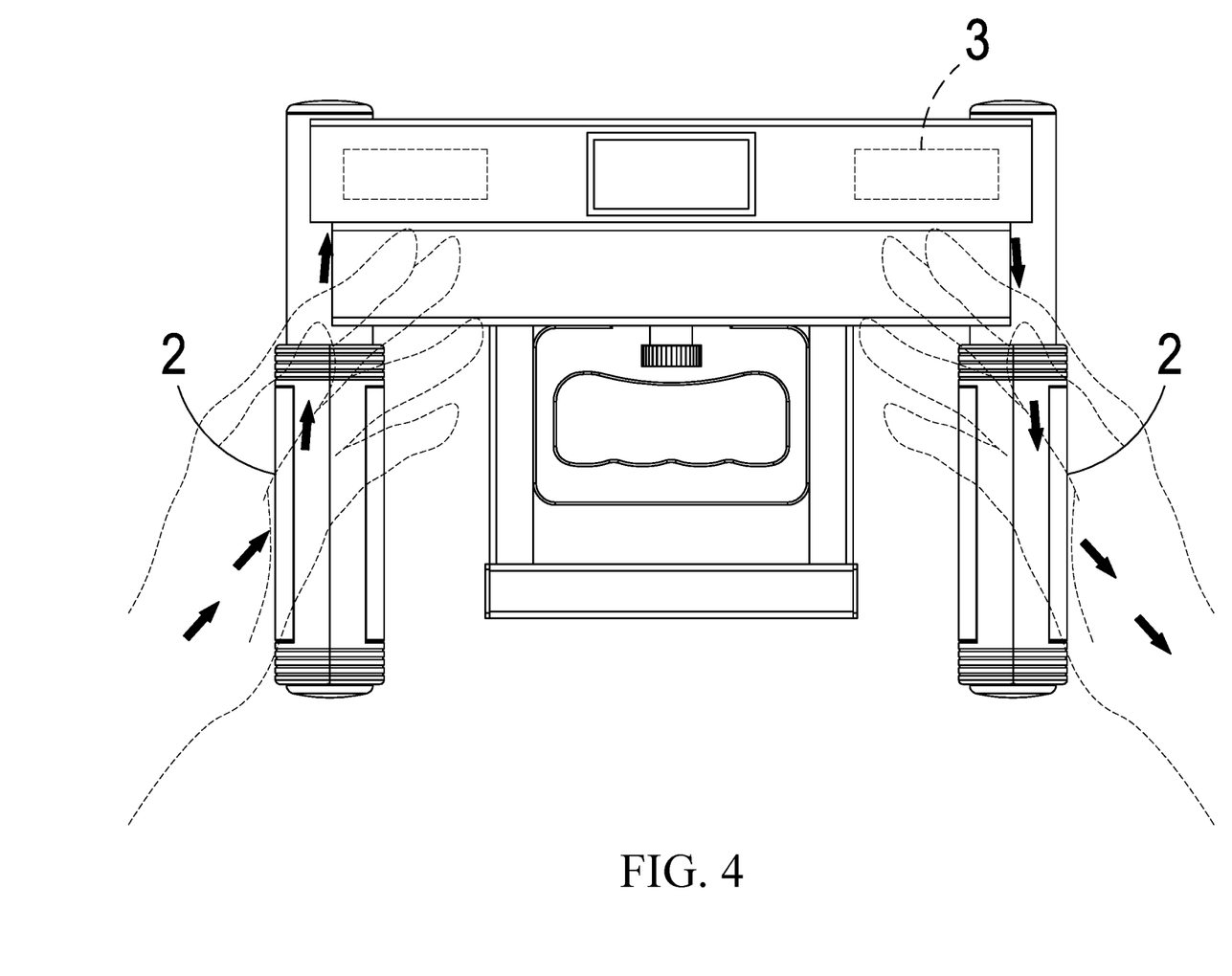
FIG. 4 is a current transfer schematic diagram of the preferred embodiment of the present invention.
Figure 5:
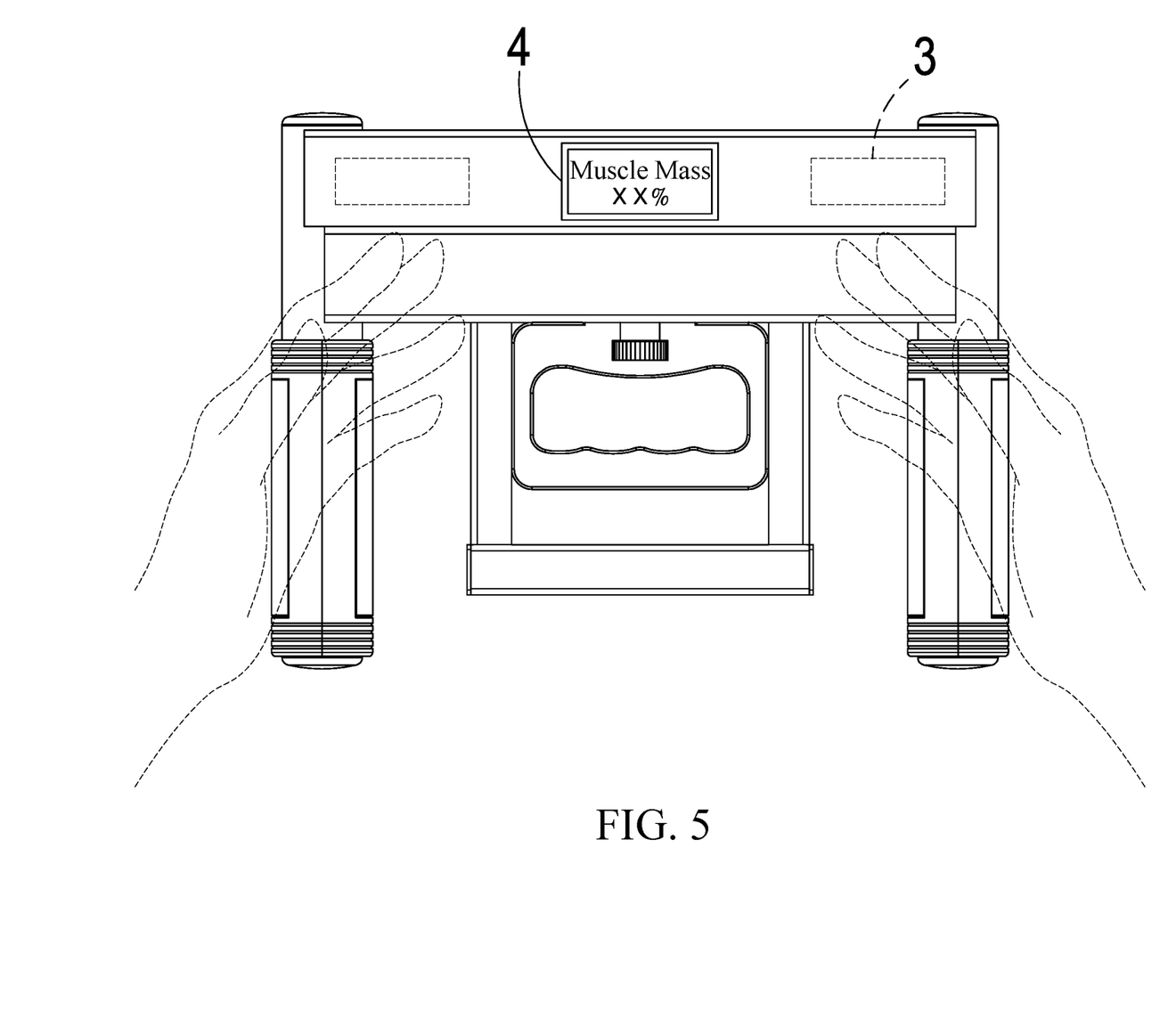
FIG. 5 is a display schematic diagram of the preferred embodiment of the present invention.
Figure 6:
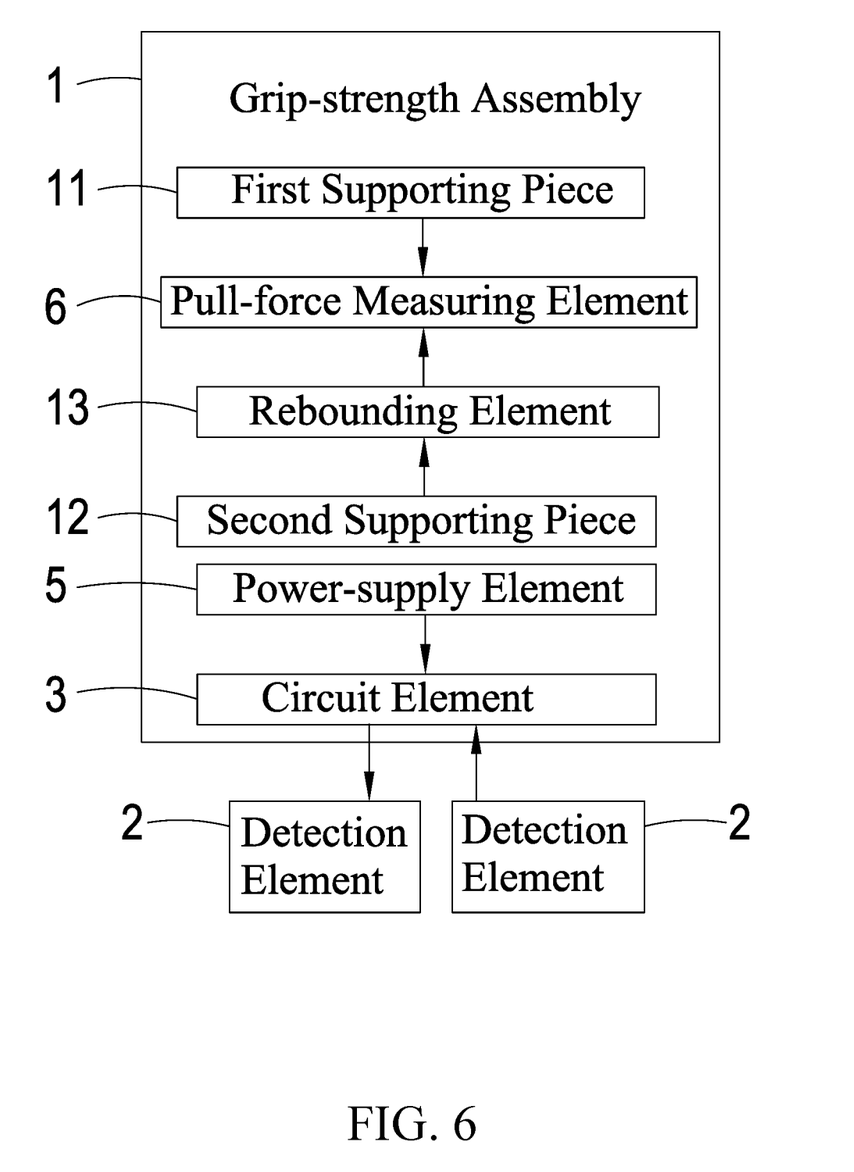
FIG. 6 is a structure block action schematic diagram of the preferred embodiment of the present invention.

Please refer to FIG. 1, which is a stereo perspective view of the preferred embodiment of the present invention; it can be clearly seen from the figure that the present invention comprises: a grip-strength assembly 1, a plurality of detection elements 2, a circuit element 3, a power-supply element 5, a display element 4, and a pull-force measuring element 6; wherein the grip-strength assembly 1 comprises a first supporting piece, a second supporting piece 12, and a rebounding element 13; wherein the first supporting piece 11 is a plastic main-body in this embodiment, and the second supporting piece 12 is a pull rod that can be pulled by a user; wherein the rebounding element 13 is a spring, and the pull-force measuring element 6 is set in the first supporting piece 11 and connected with one end of the rebounding element 13; wherein the other end of the rebounding element 13 is connected with the second supporting piece 12 and the pull-force measuring element 6 is a flexible detection piece; when the user applies the force on the second supporting piece 12, the force channel is transmitted to the pull-force measuring element 6 via the rebounding element 13 to measure the strength of the user's force; wherein the detection elements 2 is set on the first supporting piece 11 and can be respectively touched by the two hands of the user; in the embodiment, the detection element 2 is a rod-body having a conductive metal sheet-body; wherein the power-supply element 5 is also set in the first supporting piece 11 and is electrically connected with the circuit element 3, and the display element 4 is set on the first supporting piece 11 and is in information connection with the circuit element 3; wherein the circuit element 3 in this embodiment is a circuit board capable of generating a detection current to measure the ratio of fat, bone, muscle, and water in the human body, and the circuit element 3 can quantify the pull force strength given by the pull-force measuring element 6; wherein the power-supply element 5 is a battery that can supply power to the circuit element 3, and the display element 4 is a screen that can display the detection result of the circuit element 3.

With the above description, the technical structure of the present invention can be understood; and according to the corresponding cooperation of the structure, the user can detect the grip strength by using the grip-strength assembly 1 and the muscle ratio in the human body can be detected via the circuit element 3 cooperating with the detection elements 2; which the detailed explanation will be explained below.

Please refer to FIG. 1 to FIG. 6 at the same time, which are the stereo perspective view to the structure block action schematic diagram of the preferred embodiment of the present invention; When the above components are assembled, it can be clearly seen from the figures that the user can hold the grip-strength assembly 1 first and manually displace the first supporting piece 11 and the second supporting piece 12 with each other; when the first supporting piece 11 and the second supporting piece 12 are away from each other, the rebounding element 13 is stretched, and the displaced force is transmitted to the pull-force measuring element 6 (the measuring method is such that the pull-force measuring element 6 is bent and the pull force strength is detected by the angle of the bend, but it is not limited, and other types of measurement are also feasible; at this time, the pull-force measuring element 6 will judge the pull force strength and transmit it to the circuit element 3, and the circuit element 3 will numerically display the pull force strength and display it on the display element 4 (such as the grip strength XXKg); after the measurement is completed, the rebounding element 13 will give an elastic force to bring the first supporting piece 11 and the second supporting piece 12 close to each other to return to the original positions; such that the grip strength of the user can be measured via the pull-force measuring element 6 cooperating with the grip-strength assembly 1.

When the user wants to measure the muscle mass in the body, the hands can be respectively touched on the detection elements 2, and the circuit element 3 normally generates a weak detection current through the power supplied from the power-supply element 5, and the detection elements 2 will flow through the detection current given by the circuit element 3; when the user touches the detection elements 2, the detection elements 2 forms a loop with the human body, so that the detection current enters the user body from one detection element 2, and passes through the human body and then returns into the circuit element 3 via the other detection element 2; since the impedance of fat, muscle, bone, and water in the human body is different (for example, fat is less conductive, muscle and water are more conductive), when the detection current passes through the fat, muscle, bone, and water in the human body, the electrical resistance produced by fat, muscle, bone, and water is also different; therefore the circuit element 3 can calculate the ratio of fat, muscle, bone, and water by detecting the resistance generated when the current passes through the human body, and the calculation method is the same as the conventional body fat meter technology; after the circuit element 3 calculates the muscle mass, the numerical value is displayed on the display element 4 (for example, muscle mass XX %), so that the grip-strength assembly 1 can have the function of detecting the muscle mass in the human body in addition to the grip strength of the user.

Figure 7:
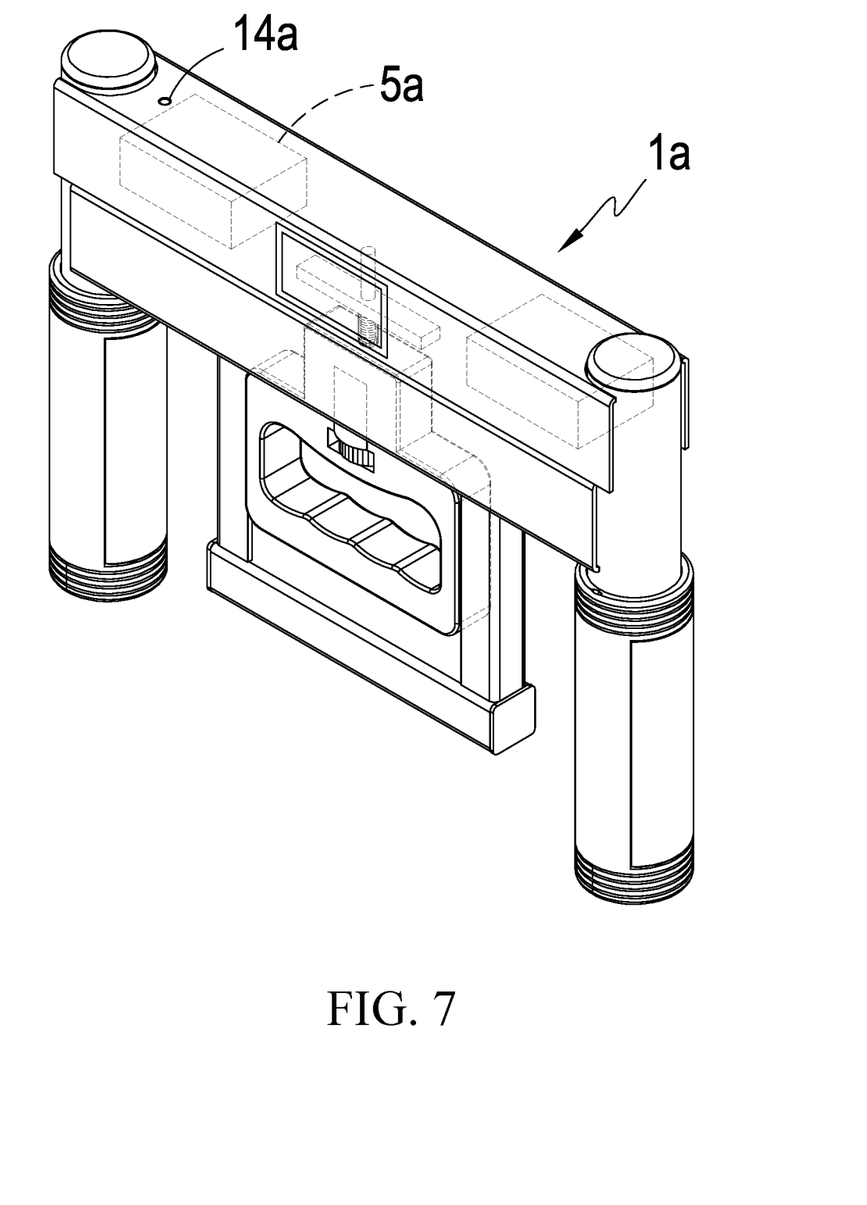
FIG. 7 is a stereo perspective view of the other preferred embodiment of the present invention.
Figure 8:
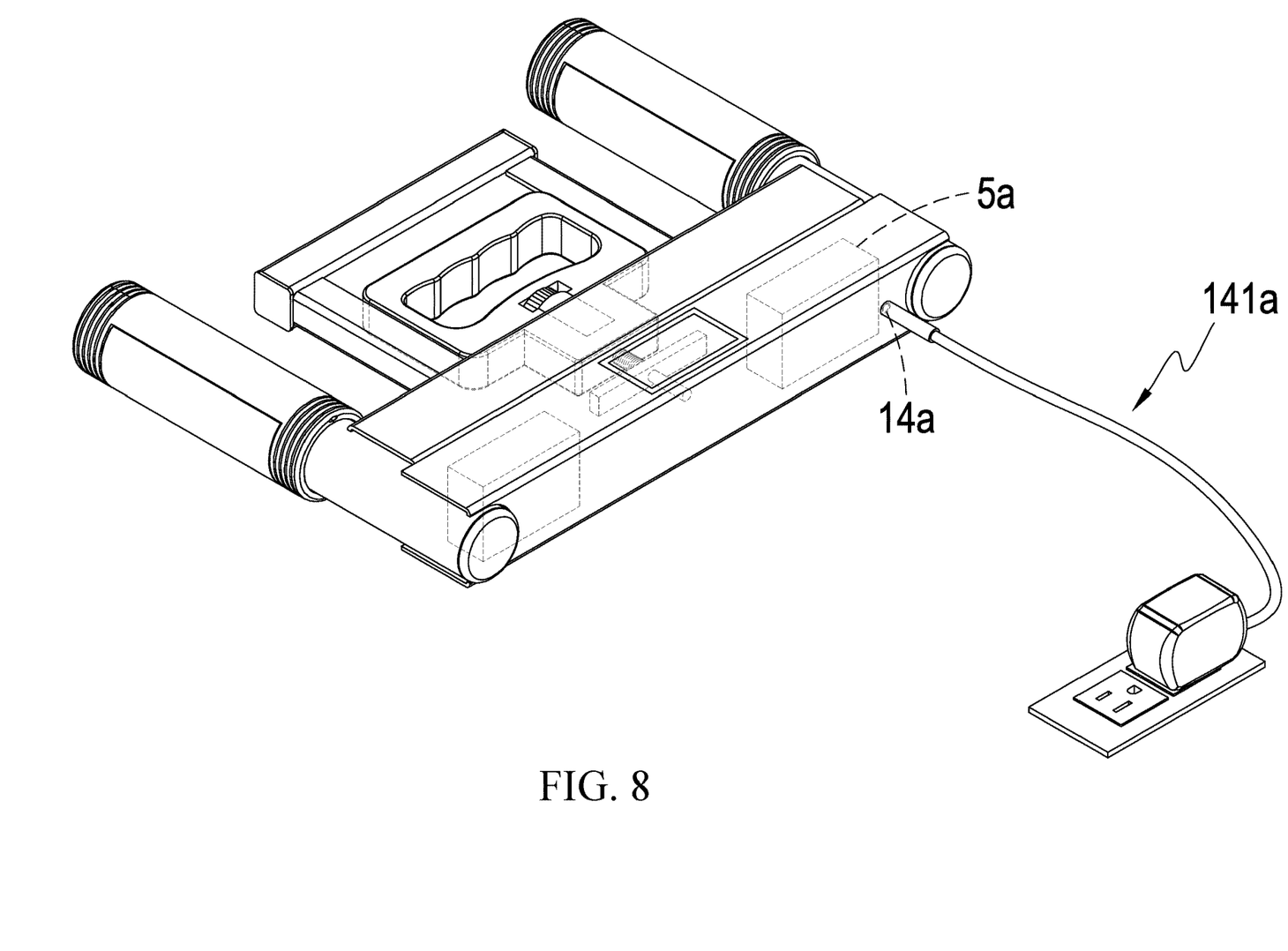
FIG. 8 is a charging schematic diagram of another preferred embodiment of the present invention.

Please further refer to FIG. 7 and FIG. 8 at the same time, which are the stereo perspective view and the charging schematic diagram of the other preferred embodiment of the present invention; this embodiment is similar to the above embodiment, the difference is only that a power connection-portion 14a is electrically connected with the power-supply element 5a and the power connection-portion 14a can be connected with an power-supply element 141a; wherein the power connection-portion 14a of this embodiment is a conventional power plug, and the power-supply element 141a is a power cord connectable to the charging device or the socket; so that the power-supply element 5a can be supplemented or given with power via the power connection-portion 14a cooperating with the power-supply element 141a.

Figure 9:
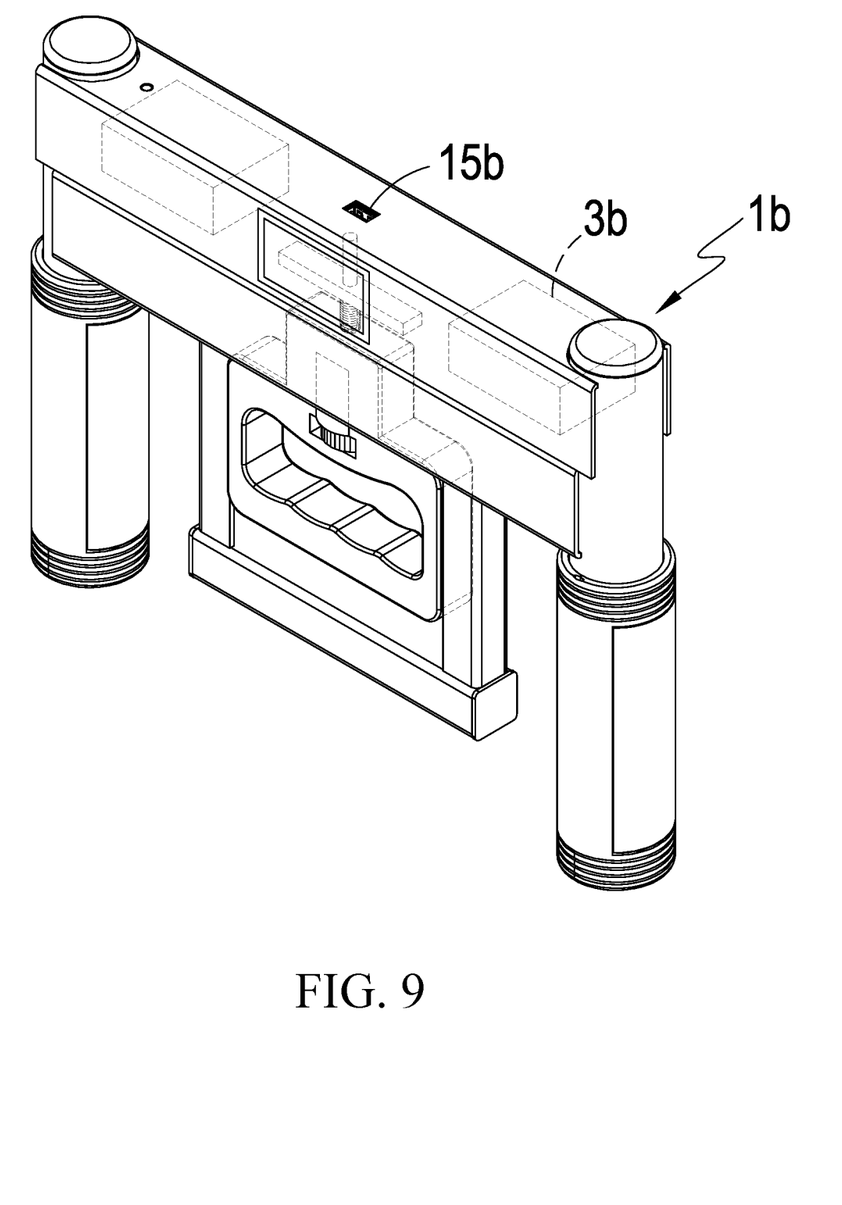
FIG. 9 is a stereo perspective view of another preferred embodiment of the present invention.
Figure 10:
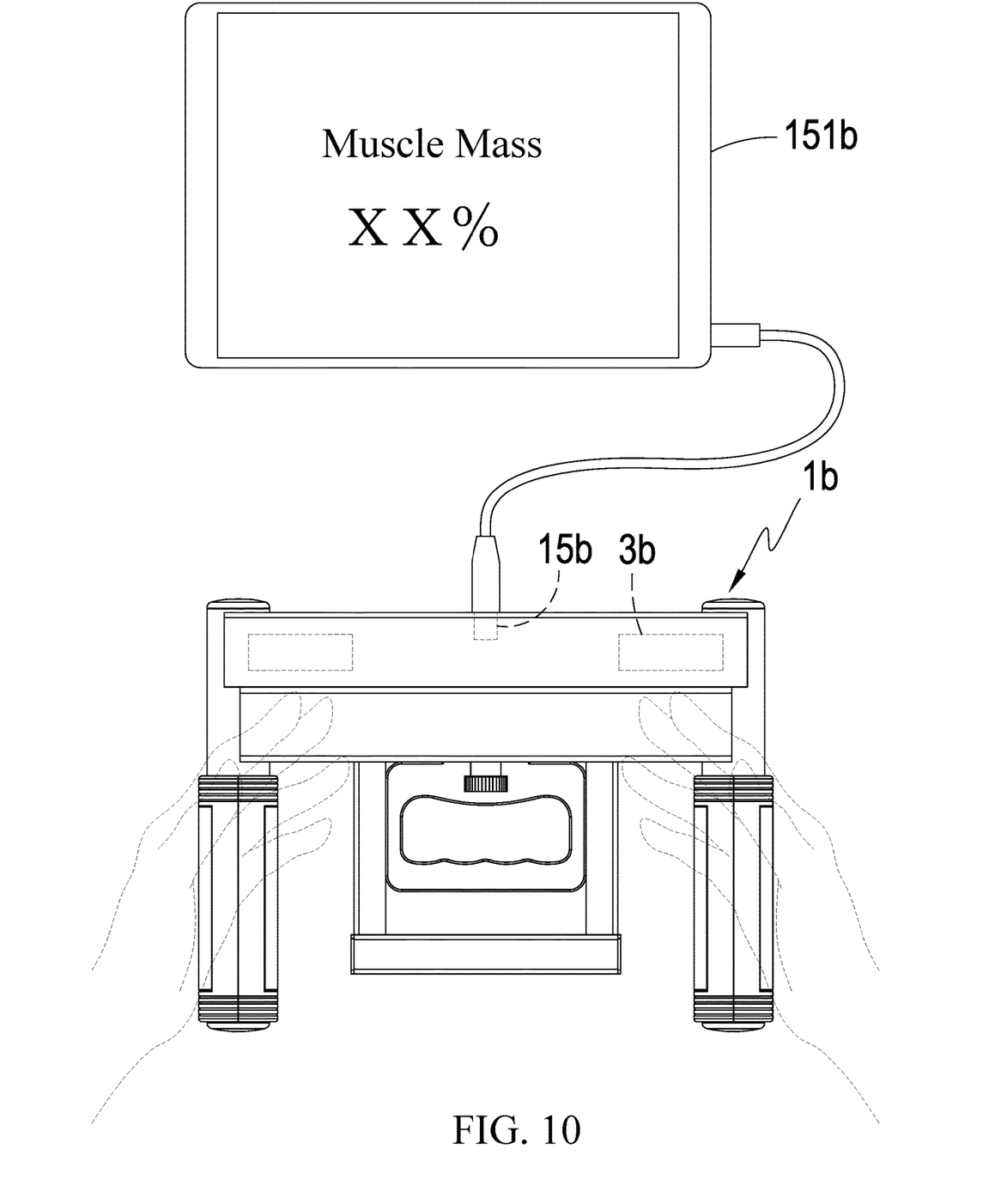
FIG. 10 is a display schematic diagram of another preferred embodiment of the present invention.

Please further refer to FIG. 9 and FIG. 10 at the same time, which are the stereo perspective view and the display schematic diagram of another preferred embodiment of the present invention; this embodiment is similar to the above embodiment, the difference is only that the grip-strength assembly 1b is set with an external connection-portion 15b and the external connection-portion 15b is connected with the circuit element 3b; wherein the external connecting portion 15b is in information connection with an electronic device 151b, and the external connecting portion 15b can connect an electronic device 151b; wherein the electronic device 151b is an electronic display, a tablet, or a mobile phone, it is not limited; such that the muscle ratio detected by the circuit element 3b can be displayed on the electronic device 151b; wherein the external connection-portion 15b in this embodiment is exemplified by a USB connector, and an electronic display can be connected by the USB connector.

Therefore, the key for the grip-strength device with detection function of the present invention to improve the conventional technology is that:

1. The user can measure the grip strength of the user via the g grip-strength assembly 1 cooperating the pull-force measuring element 6.
2. At the same time, the user can also measure the muscle mass in the body via the detection elements 2 to achieve the effect of dual functions.

We claim:

1. A grip-strength device with detection function, which mainly comprises:
    a grip-strength assembly, wherein the grip-strength assembly comprises a first supporting piece, a second supporting piece, and a rebounding element; wherein one end of the rebounding element is connected with the first supporting piece, and the other end of the rebounding element is connected with the second supporting piece;
    a plurality of detection elements, wherein the detection elements are set on the grip-strength assembly;
    a power-supply element, wherein the power-supply element is set in the grip-strength assembly;
    a circuit element, wherein the circuit element is set in the grip-strength assembly, and is in information connection with the detection elements; wherein the circuit element is electrically connected with the power-supply element to generate a detection current to the detection elements through the power given by the power-supply element, and then the detection elements receive the detection current which has pass the human body; and
    a pull-force measuring element, wherein the pull-force measuring element is set in the grip-strength assembly, and is in information connection with the circuit element; thereby measuring the displacement force when the first supporting piece and the second supporting piece are displaced with each other.

2. The grip-strength device with detection function according to claim 1, wherein a display element is set on the grip-strength assembly, and the display element is in information connection with the circuit element.

3. The grip-strength device with detection function according to claim 1, wherein the grip-strength assembly is set with an external connection-portion, wherein the external connection-portion is in information connection with the circuit element.

4. The grip-strength device with detection function according to claim 3, wherein the external connection-portion is set with an external connection-portion, wherein the external connection-portion is in information connection with an electronic device.

5. The grip-strength device with detection function according to claim 1, wherein the grip-strength assembly is set with a power connection-portion, wherein the power connection-portion is electrically connected with the power-supply element.

6. The grip-strength device with detection function according to claim 5, wherein the grip-strength assembly is set with a power connection-portion, wherein the power connection-portion is provided for connecting with an external power-supply element.

7. The grip-strength device with detection function according to claim 1, wherein the circuit element detects the muscle mass in the human body via the detection current.

* * * * *